US00PP31256P2

(12) United States Plant Patent
Kordes

(10) Patent No.: US PP31,256 P2
(45) Date of Patent: Dec. 24, 2019

(54) FLORIBUNDA ROSE PLANT NAMED 'KORROSOBI'

(50) Latin Name: *Rosa hybrida*
Varietal Denomination: KORrosobi

(71) Applicant: W. KORDES' SOHNE Rosenschulen GmbH & Co KG, Klein Offenseth-Sparrieshoop (DE)

(72) Inventor: Wilhelm-Alexander Kordes, Klein Offenseth-Sparrieshoop (DE)

(73) Assignee: W. KORDES' SOHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 15/998,032

(22) Filed: Jun. 18, 2018

(30) Foreign Application Priority Data

Sep. 20, 2017 (QZ) ..... PBR 20172305

(51) Int. Cl.
*A01H 5/02* (2018.01)
*A01H 6/74* (2018.01)

(52) U.S. Cl.
USPC ..... Plt./146

(58) Field of Classification Search
USPC ..... Plt./146
See application file for complete search history.

(56) References Cited

U.S. PATENT DOCUMENTS

PP24,406 P2 4/2014 Kordes

*Primary Examiner* — Annette H Para
(74) *Attorney, Agent, or Firm* — Buchanan Ingersoll & Rooney PC

(57) ABSTRACT

A new and distinct variety of Floribunda Rose Plant, herein referred to by its cultivar name, 'KORrosobi', is provided which forms in abundance on a substantially continuous basis attractive, orange colored blossoms. The vegetation is vigorous and the growth habit is very bushy and compact. Attractive ornamental glossy, dark green foliage is formed. The new variety is particularly well suited for providing distinctive ornamentation in the landscape.

2 Drawing Sheets

Figure 1:
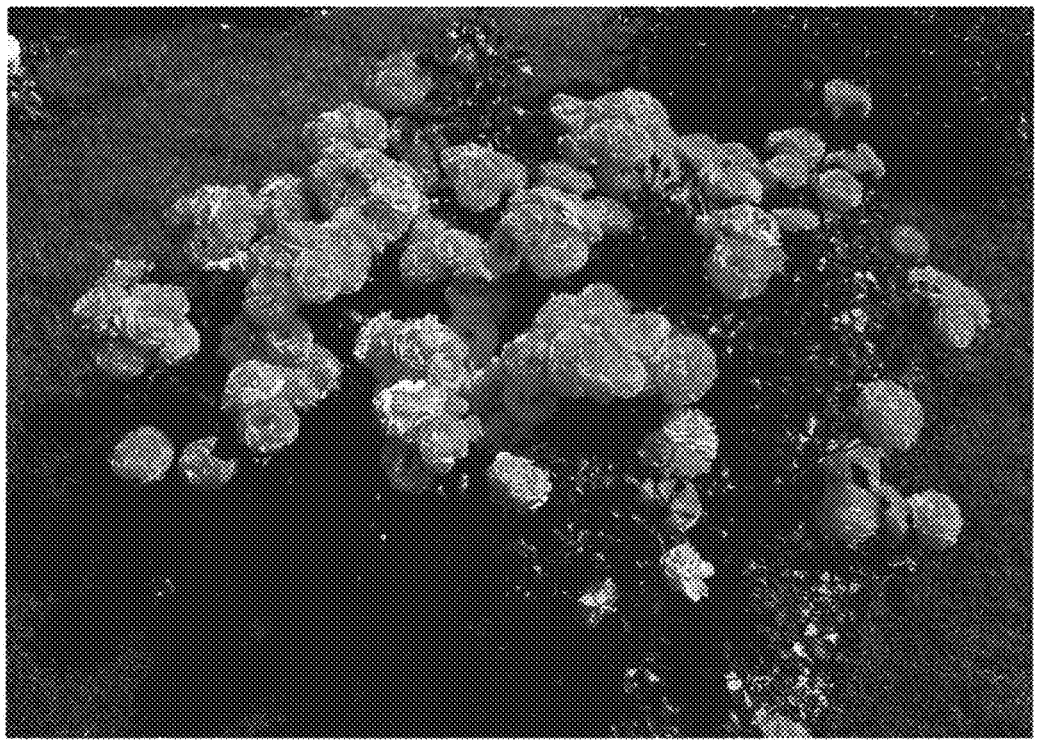

Botanical/commercial classification:
Latin name—*Rosa hybrida.*
Common name—Floribunda Rose Plant.
Varietal denomination—'KORrosobi'.

CROSS-REFERENCE TO RELATED APPLICATIONS

This application claims priority to Plant Breeders' Right Application Number 2017/2305, which was filed at Community Plant Variety Office in the European Union on Sep. 20, 2017, the contents of which are hereby incorporated by reference for all purposes.

SUMMARY OF THE INVENTION

The new variety of *Rosa hybrida* Floribunda Rose Plant of the present invention was created during May 2007 at Offenseth-Sparrieshoop, Germany by artificial pollination wherein two parents were crossed which previously had been studied in the hope that they would contribute the desired characteristics. The female parent (i.e., seed parent) of the new variety was the 'KORamflusa' variety (U.S. Plant Pat. No. 24,406). The male parent (i.e., pollen parent) of the new variety was the 'NOA75800' variety (non-patented in the United States).

The parentage can be summarized as follows:

'KORamflusa' x 'NOA75800'

The seeds resulting from the above pollination were sown and small plants were obtained which were physically and biologically different from each other. Selective study resulted in the identification of a single plant of the new variety.

It was found that the new Floribunda Rose Plant of the present invention possesses the following combination of characteristics:

(a) abundantly and substantially continuously forms attractive, orange colored blossoms,
(b) exhibits a very bushy and compact growth habit,
(c) forms vigorous vegetation, and
(d) forms attractive ornamental glossy, dark green foliage.

The new variety well meets the needs of the horticultural industry. It can be grown to advantage as ornamentation in parks, gardens, public areas, and in residential settings. Accordingly, the plant is particularly well suited for growing in the landscape.

The new variety can be readily distinguished from its ancestors. More specifically, the 'KORamflusa' variety (i.e., seed parent) exhibits larger flowers and a less compact growth habit compared to the new variety and displays yellow flowers with pink edges, whereas the new variety displays orange colored flowers. Additionally, the 'NOA75800' variety (i.e., pollen parent) exhibits a lower petal count, more disease resistance, and a different flower color compared to the new variety. Moreover, the new variety can be readily distinguished from non-parental related similar varieties. For example, the 'Poulpa1068' variety (U.S. Plant Pat. No. 28,930) displays less petals and is taller and wider compared to the new variety.

The new variety has been found to undergo asexual propagation in Klein Offenseth-Sparrieshoop, Germany by a number of routes such as budding. Asexual propagation techniques in Germany, such as budding, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORrosobi'.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately three years of age and was observed at Baden-Baden, Germany while growing outdoors on understock in June 2017.

FIG. 1—illustrates a specimen of a plant displaying floral buds and flowers at varying points of opening.

Figure 2:
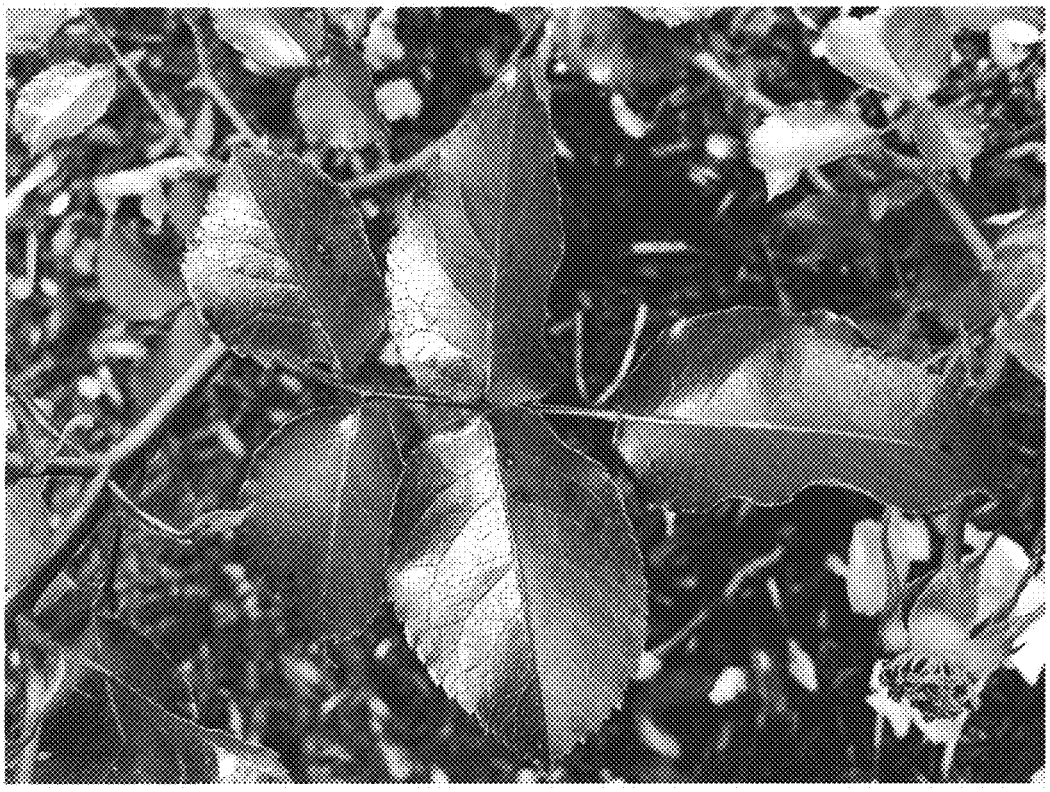

FIG. 2—illustrates a specimen of the foliage—close up view of leaflets.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a three-year-old specimen of the new variety, observed during June, while growing in a field on its own roots at Cochranville, Pa.

Class: Floribunda Rose Plant.

Plant:

*Habit*.—Very bush and compact.

*Height*.—Approximately 45.0 cm on average.

*Width*.—Approximately 45.0 cm on average.

Branches:

*Stem color*.—Old wood: commonly a blend of commonly near Yellow-Green Group 146B and Greyed-Purple Group 183B. Young stems: commonly near Greyed-Purple Group 183C.

*Main stem size*.—Length is approximately 45.0 cm on average and diameter is approximately 6.0 mm on average.

*Secondary stem length*.—Length is approximately 8.0-10.0 cm on average and diameter is approximately 3.0 mm on average.

*Thorns*.—Young thorns: length is approximately 5.0 mm on average, width is approximately 3.0 mm at point of attachment on average, and color is commonly near Greyed-Purple Group 183D. Old thorns: length is approximately 1.0 cm on average, width is approximately 8.0 mm at point of attachment on average, and color is commonly near Greyed-Purple Group 183C.

Foliage:

*General appearance*.—Ornamental glossy and dark green colored.

*Young foliage*.—Upper surface color: commonly near Yellow-Green Group 146A with near Greyed-Purple Group 183B along the margins and venation of near Greyed-Purple Group 183A. Under surface color: commonly near Yellow-Green Group 146B with some blending of near Greyed-Orange Group 176B toward the margins and venation of near Yellow-Green Group 146C.

*Old foliage*.—Upper surface color: commonly near Green Group NN137A with venation of near Green Group NN137B. Under surface color: commonly near Green Group 137B with venation of near Green Group 137C.

*Petiole*.—Upper surface: texture is smooth; color is commonly a blend of near Green Group 137B and Greyed-Purple Group 183A. Under surface: texture is smooth with a few thorns measuring approximately 2.0 mm in length, color is commonly near Green Group 137C. Length: approximately 3.5 cm on average.

*Rachis*.—Color: upper surface is commonly a blend of near Green Group 137B and Greyed-Purple Group 183A, under surface is commonly near Green Group 137C. Size: length is approximately 7.5 cm on average.

*Stipules*.—Length: approximately 2.0 cm on average. Width: approximately 6.0 mm on average. Margin: entire to erose. Color upper and under surfaces: commonly near Green Group 137C with some blending of near 185C.

*Leaf margin*.—Serrate.

*Glossiness of upper side of leaf*.—Very glossy.

Leaflets:

*Number*.—3, 5, and 7.

*Shape*.—Ovate.

*Venation pattern*.—Reticulate.

*Texture*.—Upper surface is smooth; under surface is smooth.

*Terminal leaflet*.—Length is approximately 5.0 cm on average; width is approximately 3.3 cm on average; apex is acute, base is rounded, and margin undulation is moderate.

*Lower leaflets*.—Length is approximately 3.5 cm on average and width is approximately 2.5 cm on average.

5-*leaflet leaf*.—Length is approximately 12.0 cm on average and width is approximately 8.0 cm on average.

Inflorescence:

*Number of bloossoms per stem or in a cluster*.—Typically up to 13 per stem.

*Peduncle*.—Color: commonly Yellow-Green Group 144A blended with near 199A. Diameter: approximately 3.0 mm on average. Length: approximately 4.7 cm on average. Surface texture: sparely covered in short, flexible thorns that measure less than 1.0 mm in length.

*Sepals*.—Number: commonly 5. Upper surface color and texture: covered in short pubescence and color is commonly near Yellow-Green Group 144A. Under surface color and texture: puberulent and color is commonly near Yellow-Green Group 144A blended with near Greyed-Purple Group 183C. Size: length is approximately 2.5 cm on average and width is approximately 1.0 cm on average. Margin: entire with occasional extensions on two or three sepals measuring approximately 5.0 mm to 1.0 cm in length and approximately 5.0 mm in width.

*Bud*.—Shape: rounded to ovoid. Size: length is approximately 2.0 cm on average; width is approximately 2.0 cm on average. Color (when opening): commonly near Orange-Red Group 31B blended with Yellow-Orange Group 16A.

*Flower*.—Form: double, traditional. Profile: flat to slightly concave. Depth: approximately 3.5 cm on average. Diameter: approximately 7.5 cm on average.

*Fragrance*.—Very light fragrance.

*Petal*.—Number: approximately 55 on average. Drop: good. Length: approximately 3.5 cm on average. Width: approximately 3.5 cm on average. Shape: overall shape is broadly obovate; apex is rounded; and base is rounded to cuneate. Margin: entire. Color with first and fully open: upper surface is commonly near Orange-Red Group 31B with basal spot of commonly near Yellow Group 11A; and under surface is commonly near Orange Group 26C with basal spot of commonly near Yellow Group 11D. Color when fading: upper surface is commonly near Orange-Red Group 31C with some of the outermost petals exhibiting tones near Red Group 44B near the apical margin and basal spot of near Yellow Group 11B; under surface is commonly near Orange-Red Group 31D with some of the outermost petals exhibiting tones near Red Group 44B near the apical margin and basal spot of near Yellow Group 11B.

*Petaloids*.—Number: approximately 6 on average.

*Stamen*.—Number: approximately 60 on average. Anthers: number is about 60 and color is commonly near is commonly near Yellow-Orange Group 21B. Filaments: length is approximately 5.0 mm on average and color is commonly near Yellow-Orange Group 17C.

*Pistils*.—Arrangement separate and free. Number: approximately 75. Style: color is commonly near Yellow Group 4C; length is approximately 4.5 mm on average. Stigma: color is commonly near Yellow Group 6C; diameter is commonly less than 1.0 mm on average.

*Receptacle*.—Achenes stand on the bottom and wall; diameter is approximately 1.0 cm on average, shape is urn shaped to round, color is commonly near Yellow-Green Group 144A, and surface texture is smooth.

*Pollen*.—Sparse; color is closest to Orange Group 24B.

*Hips/seed*.—None observed.

Development:

*Vegetation*.—Dark green, glossy, vigorous and strong.

*Blooming*.—Abundant and substantially continuous from spring through frost.

*Hardiness*.—Hardy to USDA Zone 6b.

*Resistance to disease*.—Very good resistance for mildew.

Plants of the 'KORrosobi' variety have not been observed under all possible environmental conditions to date. Accordingly, it is possible that the phenotypic expression may vary somewhat with changes in light intensity and duration, cultural practices, and other environmental conditions.

I claim:

1. A new and distinct Floribunda Rose Plant characterized by the following combination of characteristics:

(a) abundantly and substantially continuously forms attractive, orange colored blossoms, (b) exhibits a very bushy and compact growth habit, (c) forms vigorous vegetation, and (d) forms attractive ornamental glossy, dark green foliage; substantially as herein shown and described.

* * * * *